(12) United States Patent
Davis et al.

(10) Patent No.: US 8,364,418 B2
(45) Date of Patent: Jan. 29, 2013

(54) SOFTWARE INTEGRATED CYTOMETRIC ASSAY FOR QUANTIFICATION OF THE HUMAN POLYMORPHONUCLEAR LEUKOCYTE FCγRI RECEPTOR (CD64)

(75) Inventors: Bruce H. Davis, Clifton, ME (US); Charles Bruce Bagwell, Topsham, ME (US); Benjamin Hunsberger, Bowdoinham, ME (US)

(73) Assignee: Trillium Diagnostics, LLC, Brewer, ME (US)

( * ) Notice: Subject to any disclaimer, the term of this patent is extended or adjusted under 35 U.S.C. 154(b) by 0 days.

(21) Appl. No.: 13/297,858

(22) Filed: Nov. 16, 2011

(65) Prior Publication Data

US 2012/0084013 A1 Apr. 5, 2012

Related U.S. Application Data

(63) Continuation of application No. 11/667,277, filed as application No. PCT/US2005/041917 on Nov. 18, 2005, now Pat. No. 8,116,984.

(60) Provisional application No. 60/629,654, filed on Nov. 19, 2004.

(51) Int. Cl.
*G06F 7/00* (2006.01)
(52) U.S. Cl. .............. 702/20; 702/19; 703/11; 707/700; 436/501
(58) Field of Classification Search .................. None
See application file for complete search history.

(56) References Cited

U.S. PATENT DOCUMENTS 5,380,663 A * 1/1995 Schwartz et al. ............... 436/10
2003/0022245 A1 * 1/2003 Mills ............................ 435/7.8

OTHER PUBLICATIONS

Database Biosis [Online] Biosciences Information Service, Philadelphia, PA, US; 2003, Alpsoy E et al: "Serum of patients with Bechet's disease induces classical (pro-inflammatory) activation of human macrophages in vitro." Database accession No. PREV200300226778.*
Database Biosis [Online] Biosciences Information Service, Philadelphia, PA, US; 2002, Bachli Esther et al: "Hemoglobin Scavenger Receptor (HbSR/CD163) as Immunophenotypic Marker for Classification of Acute Myeloid Leukemia (AML)." Database accession No. P R EV200300367950.*
Ratcliffe N R et al: Immunology Letters, vol. 77, No. 3, 2001, pp. 160-174.*

* cited by examiner

*Primary Examiner* — Mary Zeman
(74) *Attorney, Agent, or Firm* — Edwards Wildman Palmer LLP; George W. Neuner

(57) ABSTRACT

The invention relates a method of quantifying CD64 and CD163 expression in leukocytes and, specifically to a kit for use with a flow cytometer including a suspension of quantitative fluorescent microbead standards, fluorescent labeled antibodies directed to CD64 and CD163, and analytical software. The software is used to take information on the microbead suspension and fluorescent labeled antibodies from a flow cytometer and analyse data, smooth curves, calculate new parameters, provide quality control measures and notify of expiration of the assay system.

1 Claim, 13 Drawing Sheets

0 = No evidence of infection or inflammation
Mean PMN CD64 (±SD) = 1,432 (±832); N = 39
Abnormal (>1,500): 36%

1 = Localized infection or tissue injury
Mean PMN CD64 (±SD) = 2,025 (±1,057); N = 19
Abnormal (>1,500): 63%

2 = Clinical finding or lab tests suspicious for systemic infection and/or moderate tissue injury
Mean PMN CD64 (±SD) = 6,995 (±6,973); N = 16
Abnormal (>1,500): 81%

3 = Documented sepsis and/or severe tissue injury
Mean PMN CD64 (±SD) = 9,867 (±11,378); N = 14
Abnormal (>1,500): 100%

Leuko64 Software:

*Value assignment of beads within software allows lot tolot standardization of CD64 Index.*

Lot comparisons without software

| Lot Comparison | Regression | r2 |
| --- | --- | --- |
| 03-003 A vs 03-003 B | y = 0.7355x + 0.0212 | 0.9996 |
| 03-003 A vs 03-007 A | y = 0.6867x + 0.0568 | 0.9956 |
| 03-003 A vs 03-004 B | y = 0.5159x + 0.0841 | 0.9984 |
| 03-003 A vs 03-003 C | y = 0.3837x + 0.0325 | 0.9958 |
| 03-003 A vs 03-007 C | y = 0.2754x + 0.0438 | 0.9884 |

Leuko64 Assay:

*Software value assignment of bead fluorescence values allows lot to lot CD163 Index standardization*

| Lot Comparison | Regression | r2 |
|---|---|---|
| 03-03 A vs 03-04 A | y = 0.9154x - 0.3291 | 0.9916 |
| 03-03 A vs 03-03 B | y = 0.7582x + 1.6349 | 0.9926 |
| 03-03 A vs 03-05 B | y = 0.3053x + 2.4133 | 0.9948 |
| 03-03 A vs 03-03 C | y = 0.4376x + 1.427 | 0.9952 |
| 03-03 A vs 03-05 C | y = 0.1718x + 1.7214 | 0.9911 |

# SOFTWARE INTEGRATED CYTOMETRIC ASSAY FOR QUANTIFICATION OF THE HUMAN POLYMORPHONUCLEAR LEUKOCYTE FCγRI RECEPTOR (CD64)

CROSS-REFERENCE TO RELATED APPLICATIONS

This application is a continuation of U.S. patent application Ser. No. 11/667,277, filed Dec. 23, 2008 now U.S. Pat. No. 8,11,984, allowed, which is the U.S. National Phase Application pursuant to 35 U.S.C. §371 of PCT International Patent Application No. PCT/US05/41917, filed Nov. 18, 2005, which claims priority to U.S. Provisional Application No. 60/629,654, filed Nov. 19, 2004. The entire contents of the aforementioned patent applications are incorporated herein by this reference.

FIELD OF THE INVENTION

This invention relates to the field of cell surface antigens and quantitation of expression, in particular CD64 and CD163, which can be quantified using flow cytometric instrumentation, fluorescent labeled antibodies, microbead standards and integrated software.

BACKGROUND

Sepsis is a significant health problem in the United States with an estimated nearly 750,000 new cases annually [1]. Sepsis is the 11th leading cause of death and the leading cause of mortality in the non-coronary intensive care unit with a mortality rate of 30-50% [1-3]. The frequency of sepsis has increased over 135% in a ten-year interval and is predicted to continue to rise with the increase in antibiotic resistance [1, 4]. In addition to the fully developed cases of sepsis, there are millions of patients on an annual basis in the U.S. alone that suffer severe infection or the clinical manifestations similar to sepsis that require diagnostic evaluation. Ironically, although treatment of sepsis has evolved in the last decades with newer therapeutic options of improved antibiotics and more novel approaches, such as inhibitors of the inflammatory response, little has changed to improve diagnosis and therapeutic monitoring [1-8]. Yet the medical detection and confirmation of patients suffering from infections or sepsis requires laboratory blood tests.

The laboratory diagnosis of infection and sepsis still relies on the same basic modalities that have been available since the 1970s or before. Clinical decisions regarding the likelihood of infection or sepsis are typically made on leukocyte counts, the presence of myeloid immature forms in the peripheral blood (bands or "left-shift"), laboratory tests for "acute phase reactants", such as C reactive protein, and clinical findings, such as fever. The cellular diagnostic parameters are typically problematic and lack specificity, particularly in infants [9, 10] and the elderly [11]. Furthermore, recent evidence indicates that leukocyte counts may have no significant influence on clinical decisions in patients with abdominal pain regarding surgery [12] and band counts provide little or no diagnostic information as to the probability of infection in a given patient [13, 14]. C reactive protein (CRP) levels, although not a new diagnostic test, have increasingly been advocated as a more objective diagnostic assay and therapeutic monitor, particularly in the neonatal and elderly population [15-19]. The advantages of CRP values, such as lack of interpretative subjectivity and improved sensitivity and specificity, are most evident in patient populations where studies have demonstrated a poor diagnostic utility of leukocyte counts and immaturity indices, such as in neonates, the elderly, and immuno-compromised patients. However, reliance on CRP values for sepsis or infection detection is also problematic in patients with co-morbid disease process. Being one of many acute phase reactants, CRP becomes elevated in any disease process with tissue injury, not just infection [16, 18, 20, 21]. Another limitation of CRP is a lack of specificity in distinguishing viral from bacterial infection. This lack of specificity as to the etiology of an infectious process has lead to the recent advocacy by some for the diagnostic utility of procalcitonin (PCT) measurements as a more specific indicator of bacterial infection [22-24]. Similarly there has been enthusiasm in the last ten years for potential diagnostic utility of cytokine levels, such as IL-6, and tumor necrosis factor (TNF) levels in septic patients [25-31]. But such studies generally have failed to demonstrate significant diagnostic utility for such tests and they additionally proved problematic due to the short half-life and sample stability of such inflammatory mediators. Molecular diagnostics have also made promises of newer approaches for early detection or prognosis, but still have fallen short due to technical limitation in turn around time, sensitivity, or cost [32, 33]. PCT, cytokines, TNF, and other molecular diagnostics currently remain experimental and none has been FDA cleared for in vitro diagnostic use to date.

The optimal diagnostic for sepsis and severe infection should be directed to early and specific changes related to the systemic acute inflammatory response. One of the major problems with the current laboratory tests for detecting the acute inflammatory response related to infection or tissue damage is the lack of specificity [14].

SUMMARY OF THE INVENTION

The invention relates a method of quantifying CD64 and CD163 expression in leukocytes and, specifically to a kit for use with a flow cytometer including a suspension of quantitative fluorescent microbead standards, fluorescent labeled antibodies directed to CD64 and CD163, and analytical software. The software is used to take information on the microbead suspension and fluorescent labeled antibodies from a flow cytometer and analyse data, smooth curves, calculate new parameters, provide quality control measures and indicate the expiration of the assay system.

The integrated software-fluorescent microbeads standards system is a powerful tool for monitoring, optimizing fluorescence intensity measurements and increasing sensitivity. The integration of software, quantitative standards, and fluorescent-labeled antibodies allows for improved reproducibility in measurements of CD64 and CD163 on leukocytes between different production lots of the assay system. An entire calibration and analysis can be completed in less than five minutes, and a summary report generated on a printer. All results are automatically recorded in a cumulative file history to provide comprehensive documentation of an instrument's performance.

The software is matched to specific lots of microbead standards and fluorescent-labelled mixtures of monoclonal antibodies, since all fluorescent molecules are subject to degradation and variability in conjugation efficiencies between production lots. Thus, for each batch of microbeads and fluorescent reagents, the associated software program includes information on the fluorescence intensity of each population of microbeads within the batch. When the kit approaches its expiration date, the software alerts the operator and further interrogates the users to verify the assay lot in use and the type of flow cytometric instrument employed as part of the specimen analysis. One of the novel features of this invention is that standardization between production lots is monitored and calibrated through the use of biologic specimens, specifically human blood samples with leukocytes of varying levels of CD64 and CD163 expression. The bias or difference in leukocyte CD64 and CD163 expression between different production lots is normalized by a factor determined by regression analysis between lots and changes in the fluorescent value assigned to the microbeads within the software. These monitoring comparisons of different production lots of the assay kit done on different biologic samples will determine whether the microbeads are within the required range of fluorescence intensity to insure levels of imprecision between assay lots of $\leq 5\%$. Daily calibration of flow cytometers using the microbeads and software of the invention allows objective comprehensive monitoring of fluorescence intensity without complications due to reagents, cell preparation techniques, operating conditions, or stained cell samples. Once the calibration is done, the actual amount of fluorescent antibody bound by the specimen cells may be determined through the use of external standards, such as SRM 8640 produced by the National Institute of Standards and Technology (NIST). This measurement may be used to calculate the number of CD64 molecules (receptors) using fluorescent labeled antibodies or determine an index of antigen expression that is comparable to absolute molecular expression, which in turn, is useful in early diagnosis of infection.

In particular, the invention includes a kit for automated performance analysis to quantify CD64 and CD163 expression in a leukocyte and calibration for a flow cytometer, said kit used with a flow cytometer or a blood cell counter with fluorescence detection capabilities, blood specimens, a programmable computer and a display screen, said kit comprising:
(a) at least one or more monoclonal antibodies directed to CD64 conjugated to fluorescein isothiocyanate (FITC) or similar fluorochrome;
(b) at least one or more monoclonal antibodies directed to CD163 conjugated to phycoerythrin or similar fluorchome;
(c) a suspension of microbeads having reliable fluorescence stability over a finite period of time;
(d) at least one or more fluorochromes, said fluorochrome having a useful life, said useful life being designated in said kit; and
(e) software operating on said computer comprising 1) information on the fluorescence intensity of each fluorescent reagent and microbeads, said software operating with said computer to control calculation of calibration and fluorescence information tailored to said microbeads, and display on said screen an expiration date correlated to the useful life of said microbeads to an operator calibrating said flow cytometer with said microbeads, wherein said software ceases operation on said computer if the operator does not accurate acknowledge the instrument model and correct assay kit with an expiration time, whereupon said flow cytometer cannot be calibrated with said software and said microbeads and the operator must utilize another suspension of microbead populations and software tailored for use on said computer with said another suspension to calibrate the flow cytometer; 2) the ability to acquire data on blood specimens using fluorescence, forward angle light scatter ("FS") and side or wide angle light scatter ("SS") and thus automatically gate or identify specific cell subpopulations, smooth the data, locate peaks in fluorescence intensity corresponding to each microbead and cell specific populations, construct linear regression plots' determine the fluorescence threshold intensity of the flow cytometer, and create histograms or graphic displays; 3) the ability to find cell specific clusters using iterative cluster finding algorithms; 4) the ability to perform automated data normalization; and 5) the ability to calculate the CD64 and CD163 indices.

Thus, the CD64 assay of the present invention represents a significant improvement in the diagnosis, therapeutic monitoring, and management of individuals of all ages with serious infections. Another equally significant societal benefit of the CD64 assay is that by providing a more sensitive and specific assay of the human sepsis and infection, there should also be a secondary effect of reducing the spread of antibiotic resistance of bacteria, a growing worldwide health concern.

Other and further aspects, features and advantages of the present teachings will be apparent from the following description of the various embodiments of the present teachings given for the purpose of disclosure.

DETAILED DESCRIPTION OF THE INVENTION

Figure 1:
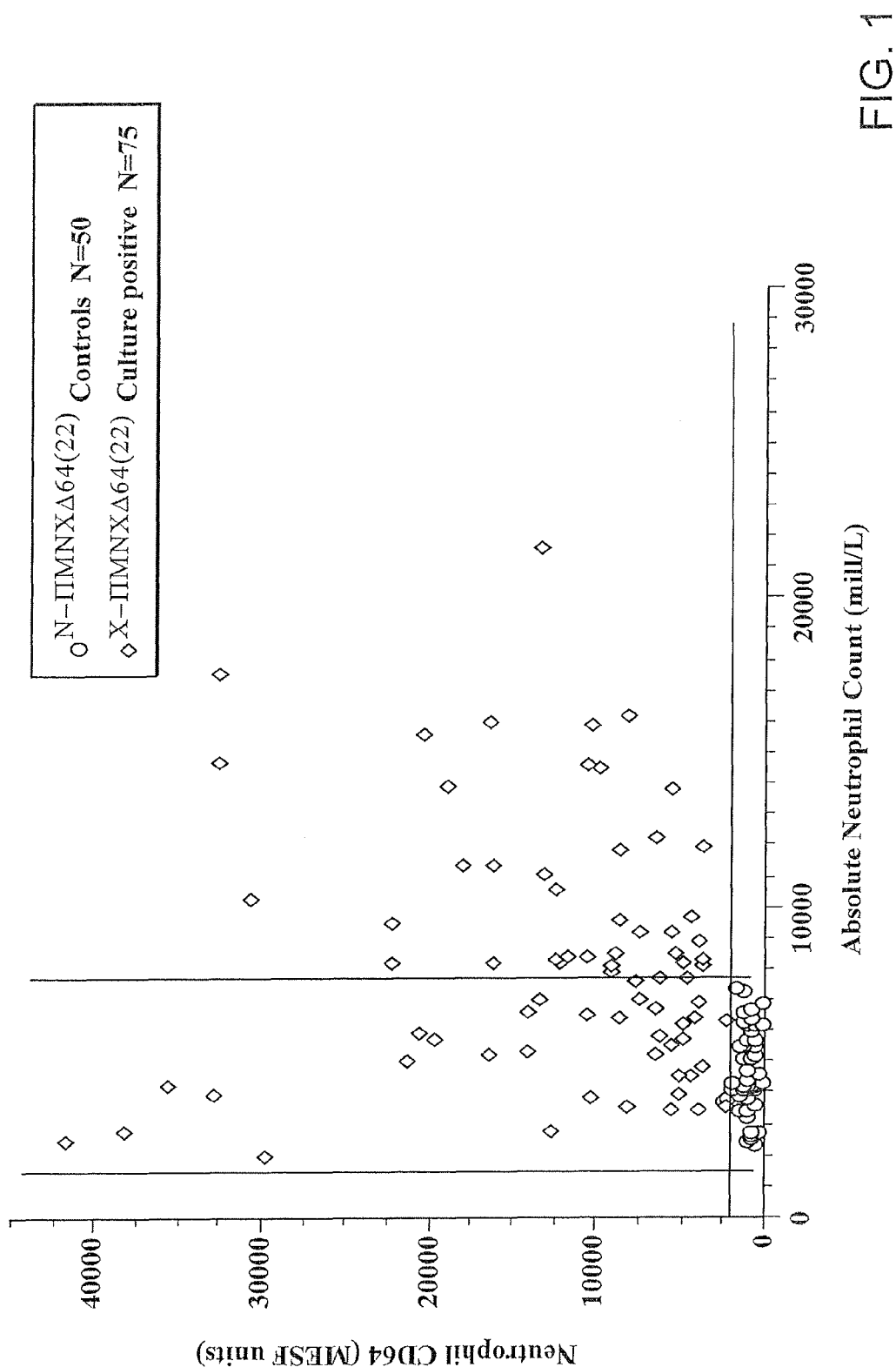
FIG. 1 is a diagrammatic representation of PMN CD64 expression in patients with culture proven infection (diamonds) are elevated in over 97.5% of individuals compared to the normal low value seen with healthy controls (circles); PMN CD64 values do not correlate with the neutrophil leukocyte count and are increased in those patients with infection, but normal neutrophil count.

The inventors of the present invention and others have reported clinical studies indicating that PMN CD64 expression represents a specific diagnostic indicator of an active acute inflammatory response [34-43]. Unlike many other activation related antigenic changes on neutrophils (PMN) and other leukocytes, such as CD11b, CD18, CD16, CD45RA, and CD62L, neutrophil CD64 has negligible expression in the health individual and shows no evidence of sensitivity to blood sample manipulation [35, 37]. In contrast to many other myeloid antigens, such as CD16 or CD11b, PMN CD64 expression in both healthy individuals and those with upregulated CD64 expression is not altered by cell activation by chemotactic factors, PMA, or in vitro exposure to bacteria [35, 37, 38, 44, 45]. Additionally the expression of PMN CD64 is stable in anti-coagulated blood samples for up to 48 hours [35, 45]. Additionally previous studies by Trillium have shown normal levels of CD64 during otherwise healthy pregnant women, in contrast to other PMN and monocyte antigens, such as CD11b, CD14, CD32, and CD62L, which have been reported to show a significant change in women during pregnancy [46, 47]. Thus indicating the PMN CD64 measurements are practical as a diagnostic test, allowing performance in any laboratory setting for both outpatients and inpatients. PMN CD64 up-regulation by inflammatory related cytokines, such as G-CSF and interferon gamma (IFN-γ) occurs in a the short time scale of 4 to 6 hours for cell surface expression and 1 to 3 hours for detectable mRNA increases by Northern blot analysis [35, 40, 48-50]. This upregulation of PMN CD64 appears to directly correlate with enhanced bactericidal [40] and anti-fungal [51] activity. Thus, given that normal neutrophil expression of CD64 is less than 1000 sites per cell and that detectable up-regulation can be found within 4 to 6 hours after an acute tissue injury, dissemination of infection, or administration of recombinant interferon gamma or G-CSF, early diagnosis is possible. Therefore, PMN CD64 quantitation represents an ideal candidate as an improved diagnostic compared to leukocyte counts, myeloid immaturity assessment, and acute phase reactants for the reasons listed in Table 1 and data in FIG. 1. In summary, quantitative PMN CD64 measurements offer the potential to be the first, clinically useful diagnostic cell-based parameter of a systemic acute inflammatory response.

TABLE 1

Rationale for clinical utility of PMN CD64 assay.

PMN CD64 expression is negligible in the healthy state and increases under the influence of inflammatory related cytokines (IFN-γ, IL-12, G-CSF)
Increased PMN CD64 expression results in enhanced antibody-mediated functional responses (phagocytosis, oxidative burst, bactericidal activity) in PMNs-pathophysiologically significant change
Measurements stable in routinely collected and handled anti-coagulated blood samples for 30 hours at room temperature and 48 hours refrigerated
Assay performed within one hour, requires small volume, batch analysis possible
PMN CD64 increase highly correlated with sepsis, infection or systemic acute inflammation TABLE 1-continued Rationale for clinical utility of PMN CD64 assay.

Figure 2A:
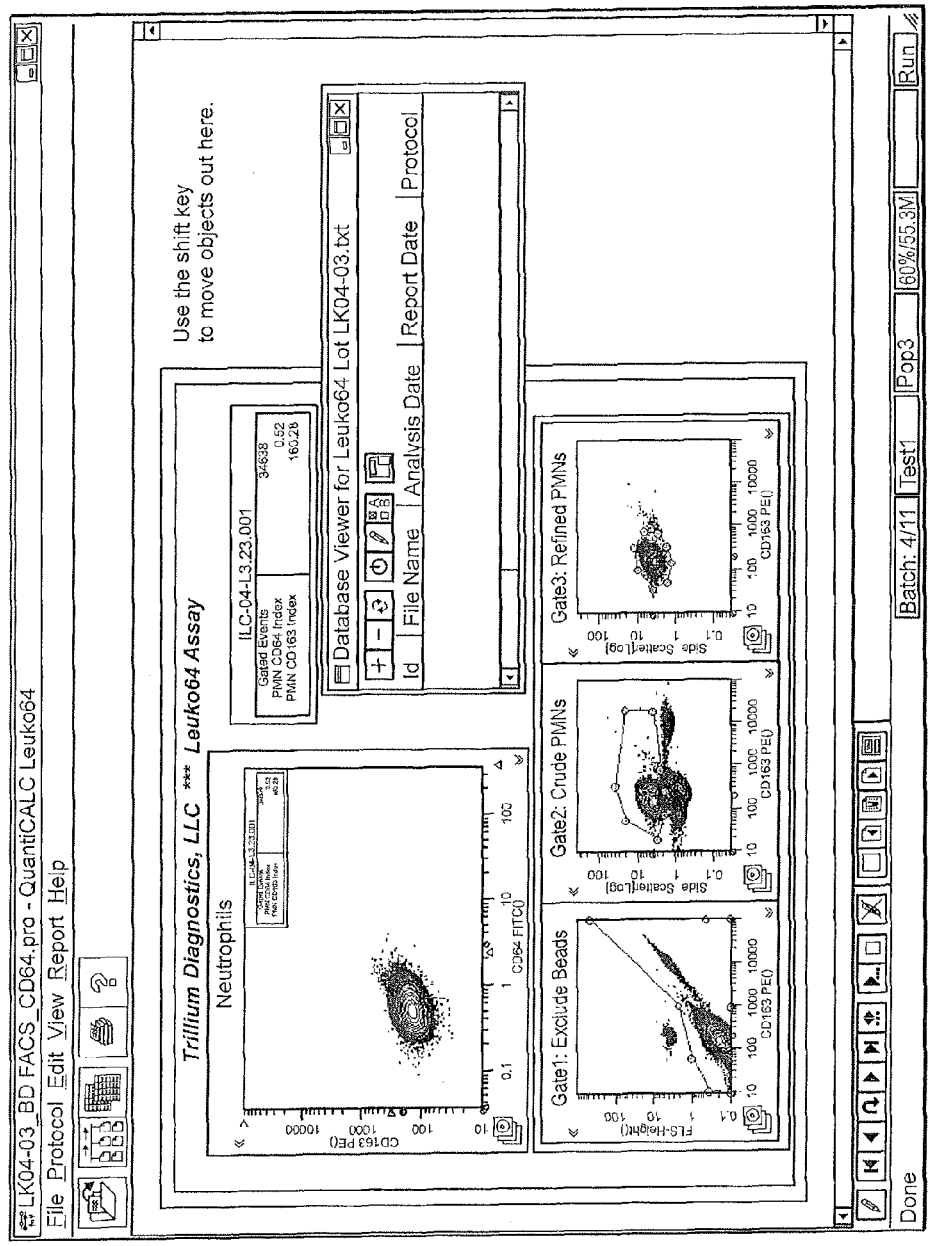
FIG. 2 represents flow cytometric analysis of human blood sample with normal (top panel—FIG. 2A) and elevated (bottom panel—FIG. 2B) neutrophil CD64 quantified using bead calibrators to derive PMN CD64 Index units; the other blood leukocyte populations of lymphocytes, monocytes, as well as neutrophils (shown in gated region in figure) are identified through software data analysis using iterative cluster finding algorithms and both anti-CD64 FITC and anti-CD163 PE staining of the samples.
Figure 2B:
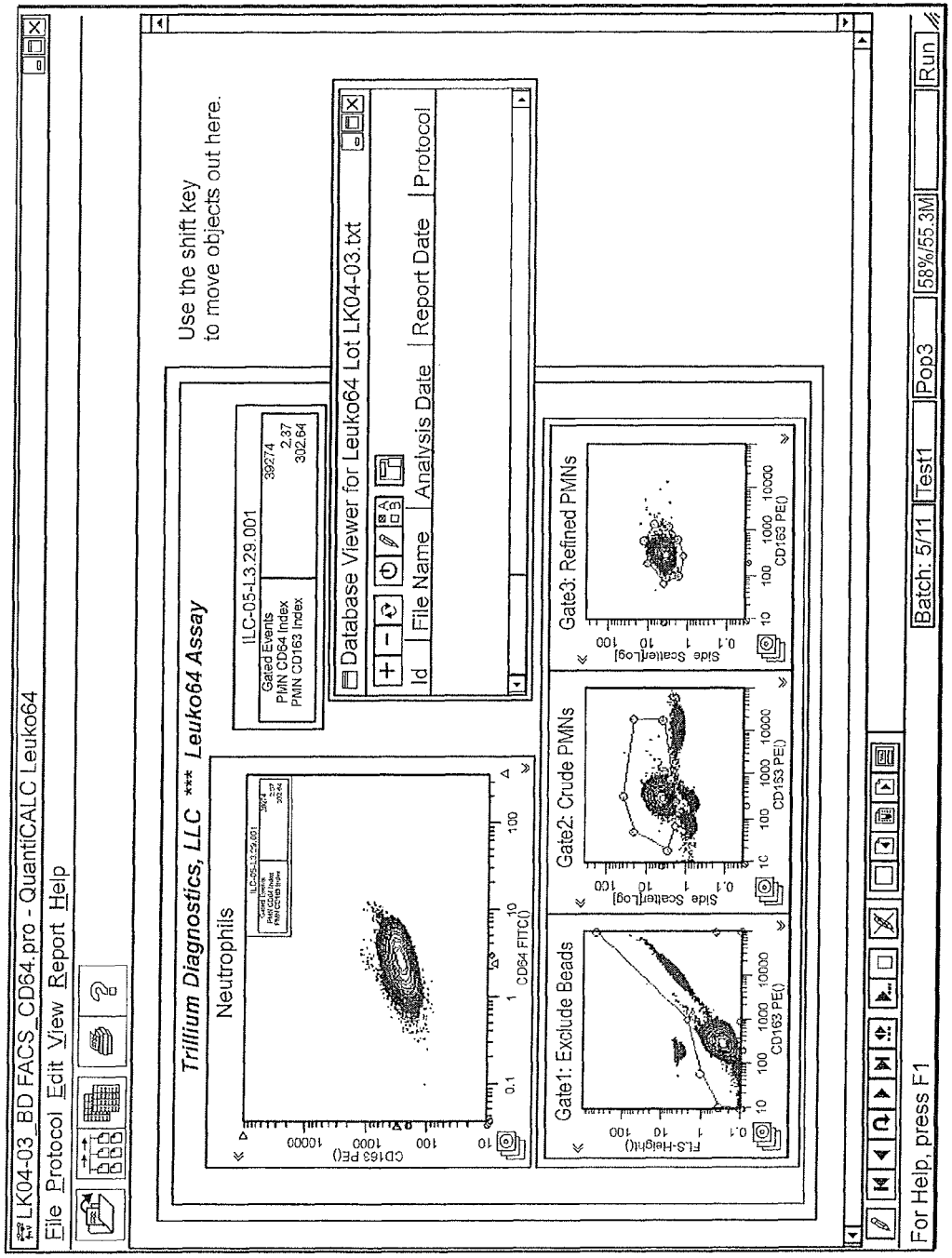
Figure 3A:
FIG. 3 demonstrates the software analysis of samples where the defined internal cellular controls to not "pass" or demonstrate the expected result of lymphocytes lacking CD64 expression (top panel—FIG. 3A), which is typically due to improper instrument set-up or addition of incorrect reagents, and monocytes lacking significant expression of CD64 (bottom panel—FIG. 3B), which is usually the result of insufficient anti-CD64 reagent added to the blood sample. The automated flags or popup boxes alert the user to problems with the technical performance of the assay.
Figure 3A:
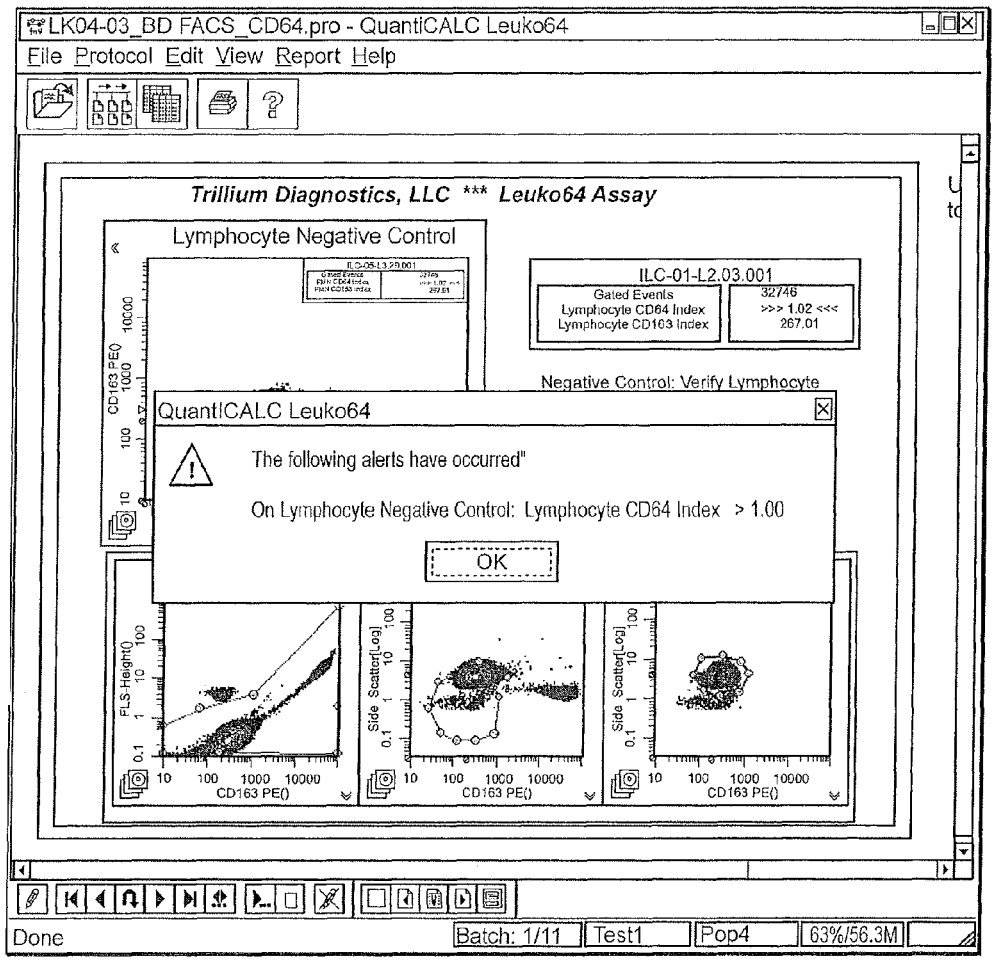
Figure 3B:
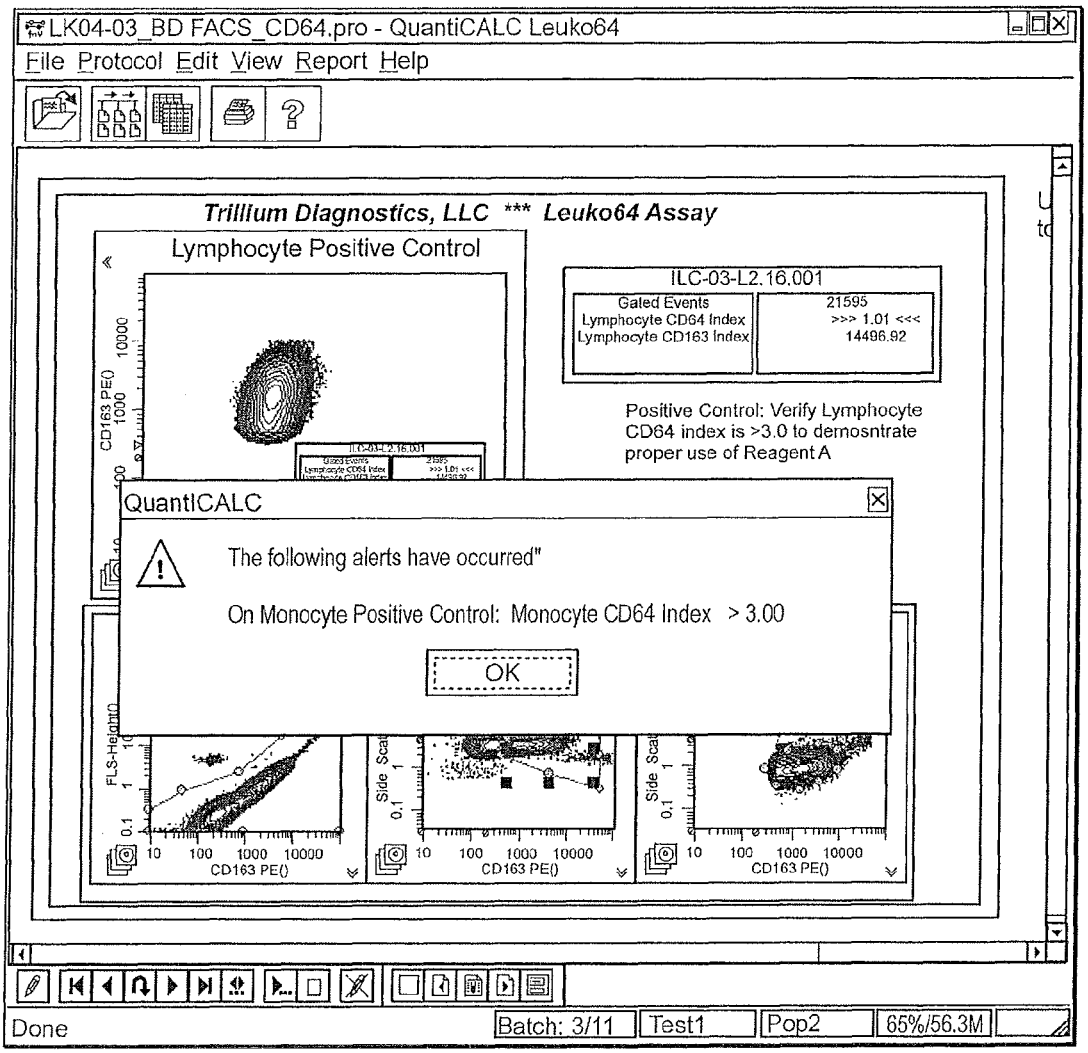

Level of PMN CD64 barometer of systemic inflammatory response-potential for therapeutic monitor role in antibiotic use
CD64 up-regulation not surrogate for absolute neutrophil count, band count, CBC instrument flagging, Sedimentation Rate, C reactive protein
Patients of all ages and immuno-suppressed conditions capable of CD64 up-regulation
High specificity-PMN CD64 expression is not elevated in:
Malignancy of myeloid cells (CML. MPD, MDS)
Any drug therapy (other than cytokines)
Clinical conditions with localized tissue damage (myocardial ischemia, uncomplicated surgery, and exercise injury)
Pregnancy Flow cytometric quantitative techniques have been the methodology employed in the majority of studies looking at CD64 expression in myeloid cells. This instrumentation, although considered a high complexity form of clinical testing, is currently available in university medical centers, large tertiary care community hospitals, and reference diagnostic laboratories in the U.S. and most industrialized countries. The methodology most refined with regard to clinical applications has been developed by the inventors of the present invention, and have validated a whole blood lysis technique using directly conjugated anti-CD64 and standardized fluorescence bead calibrators [35, 37, 40, 52, 53]. The current methodology requires 50 µl or less of whole blood, thus being amenable to testing of patients of all ages. The assay precision has been validated on replicates as having a coefficient of variation of less than 5% [35], thus being quite competitive in precision with other clinical laboratory assays (FIGS. 2, 3).

Figure 4A:
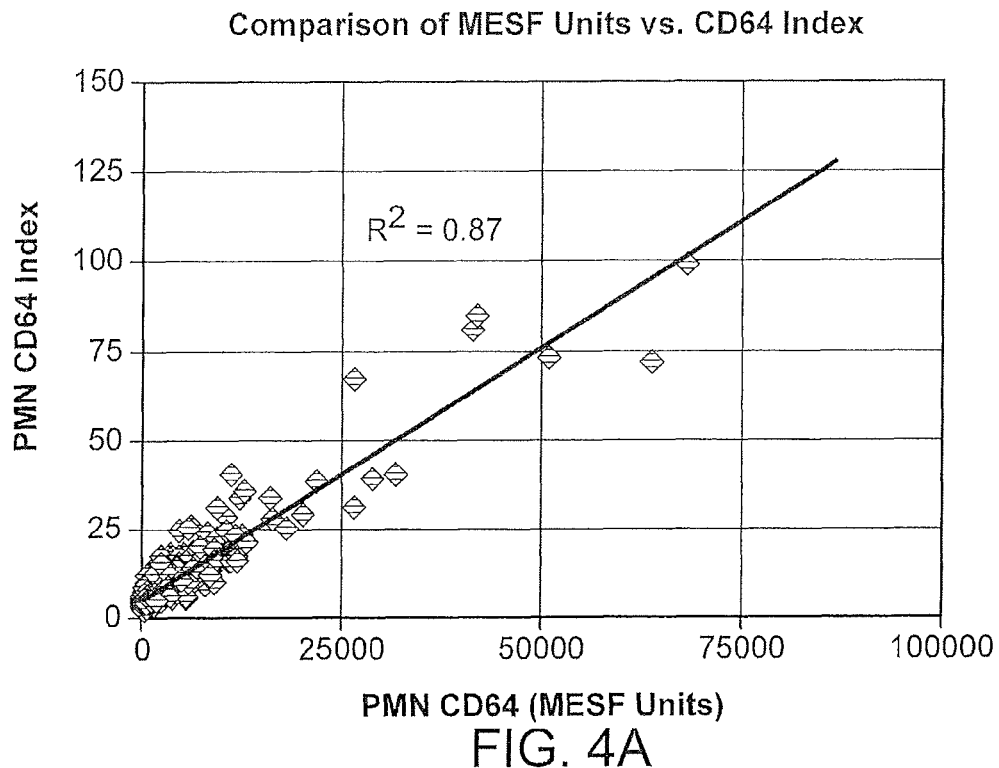
FIG. 4 illustrates the excellent correlation of the Trillium PMN CD64 index to the bead calibrated method of measuring PMN CD64 expression using MESF units is seen in two separate clinical studies (FIGS. 4A and 4B).
Figure 4B:
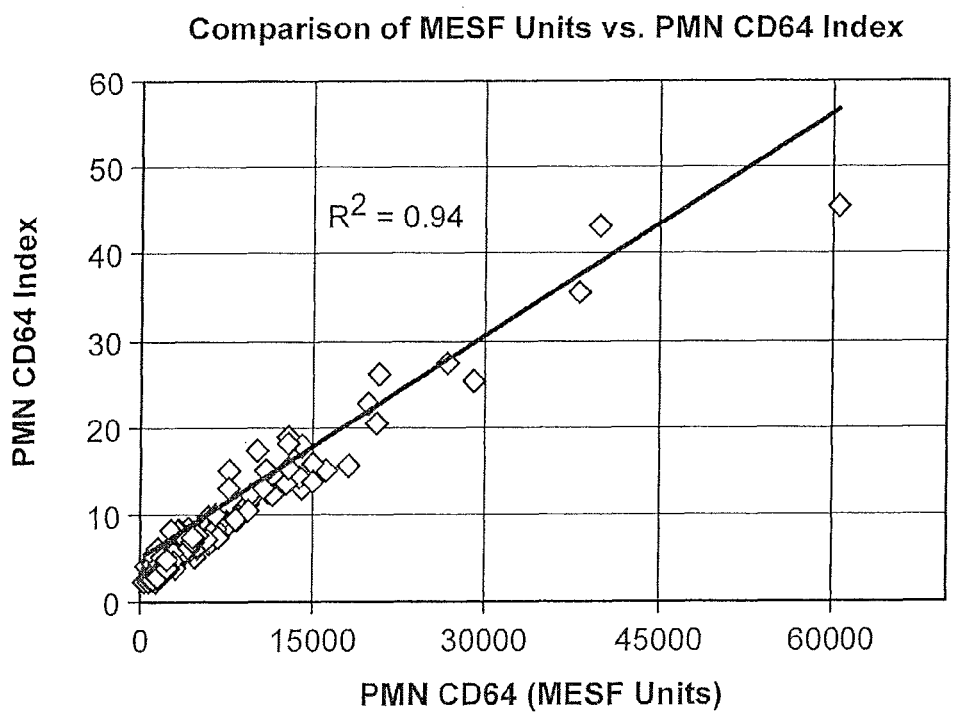

Of equal practical importance for a clinical diagnostic test, the quantitative PMN CD64 results are stable at least 30 hours at room temperature and up to 72 hours for anticoagulated blood held at refrigerated temperatures. The results can quantified in terms of mean equivalent soluble fluorescence units (MESF) derived from the difference between binding of CD64 monoclonal antibody and isotype control antibody run under parallel conditions. The day to day and assay to assay results are calibrated through the use of Quantum 26 FITC beads (formerly Flow Cytometry Standards, San Juan, PR, now Bang Labs, Fishers, Ind.) and computer data analysis with Leuk64 software (Verity Software House, Topsham, Me.). Alternatively with accurate fluorochrome to protein (F/P) ratio determinations of the monoclonal antibody reagent, the MESF units can be converted to actual average antibody binding or antigen (if the monoclonal reagent is monomeric) sites per cell. The problem with these approaches is that, although the flow cytometric assays for CD64 using beads for quantitation are sensitive and relatively precise, the cost and technical time and complexity required for a PMN CD64 clinical assay is relatively high (>$50 per test) and are subject to measurement imprecision between lots of beads and antibodies. The present invention is a novel method of quantifying PMN CD64 expression, which appears to be equivalent to previous flow cytometric bead assays with less cost to the assay and marked reduction in lot to lot imprecision. The novel method for CD64 quantitation, termed the PMN CD64 Index, is based upon a ratio of the anti-CD64 antibody binding on neutrophils to lymphocytes, a leukocyte cell population lacking CD64 expression, or to a microbead suspension. Progress to date indicates the PMN CD64 Index is substantially equivalent to the more complex CD64 quantitation using bead calibrators (FIG. 4).

Figure 5:
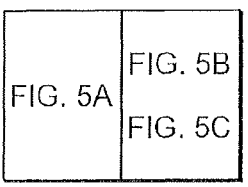
FIG. 5 illustrates that the level of PMN CD64 (FIG. 5C) is correlated with the clinical impression in patients seen in a hospital emergency room (lower left), suggesting a role in the CD64 assay in screening for a systemic inflammatory reaction and triaging patients to the appropriate medical management setting and therapy; the same degree of correlation between clinical score (defined in lower right) and neutrophil count (FIG. 5A) or CRP levels (FIG. 5B) was not observed in the same study (upper left and right).
Figure 5A:
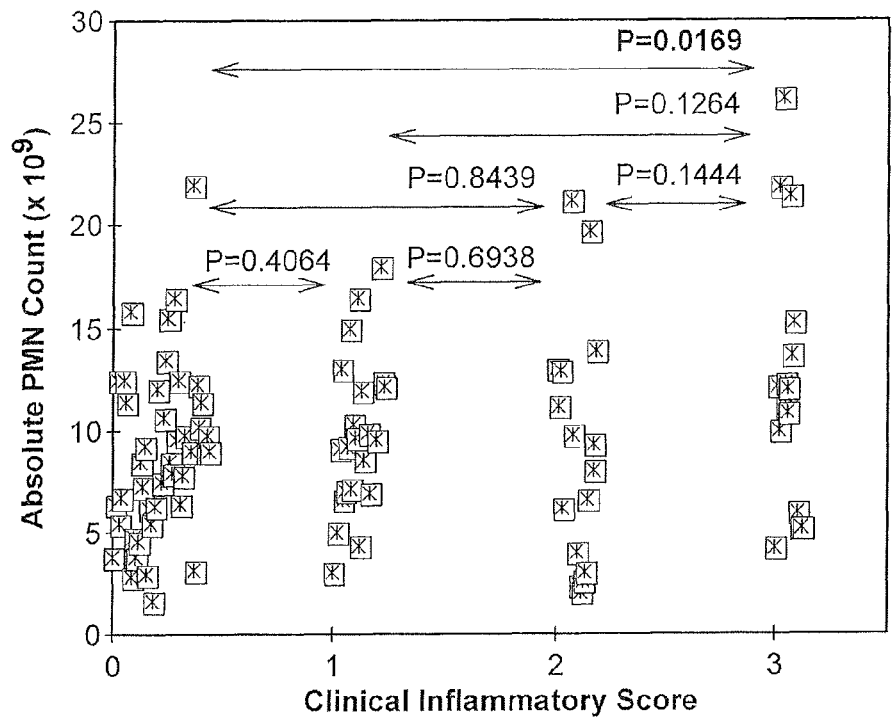
Figure 5B:
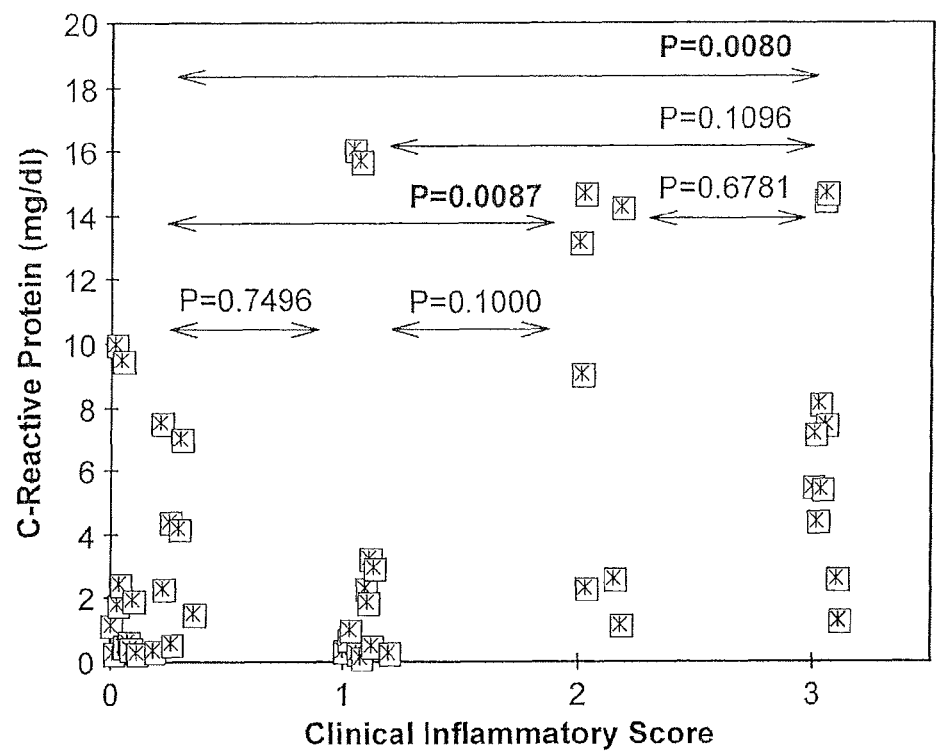
Figure 5C:
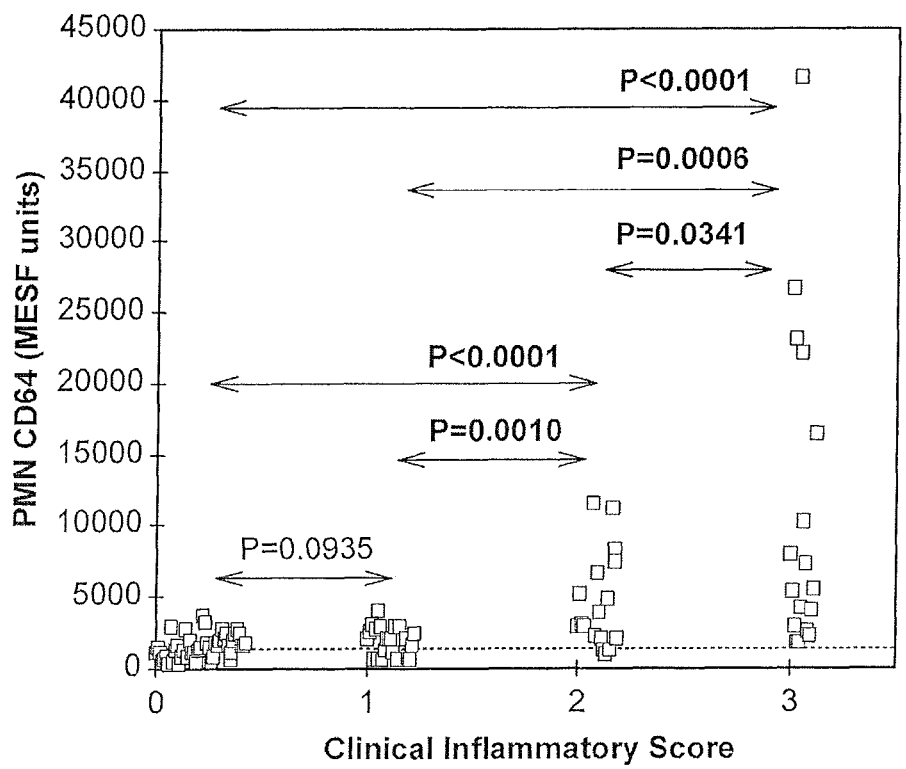
Figure 6:
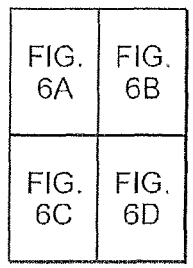
FIG. 6 illustrates the that interlot correlation is high, but that there is a difference in the PMN CD64 index due to differences in the microbead fluorescence and antibody fluorochrome conjugation efficiency (upper left panel—FIG. 6A). However the invention of using the Leuko64 software to assign microbead fluorescence values based upon interlot comparison on multiple biologic blood samples allows for good interlot correlation as well as a low interlot imprecision (upper right panel—FIG. 6B). The invention also allows for the same improvement of interlot imprecision for the monocyte CD163 index with the software (lower panels—FIGS. 6C, 6D).
Figure 6A:
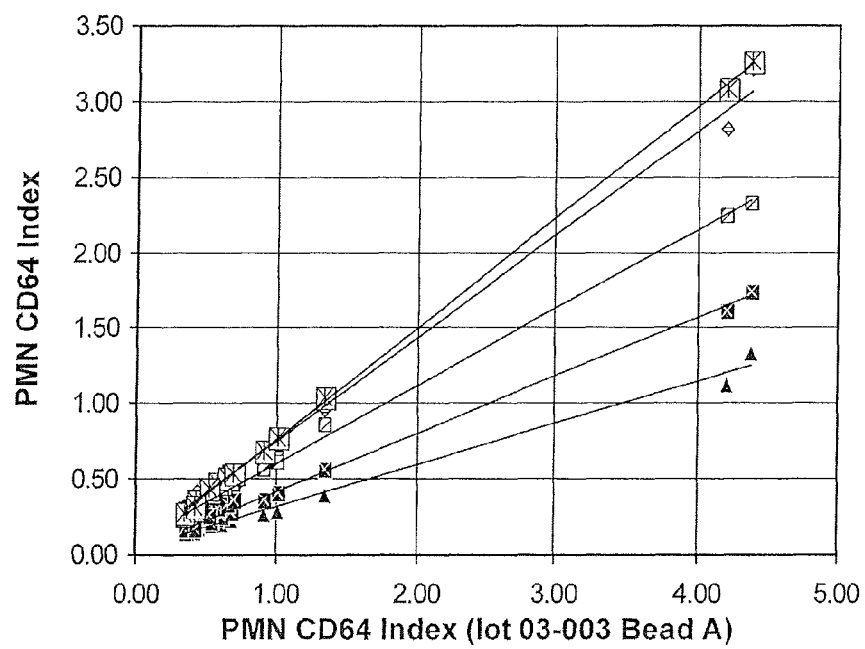
Figure 6B:
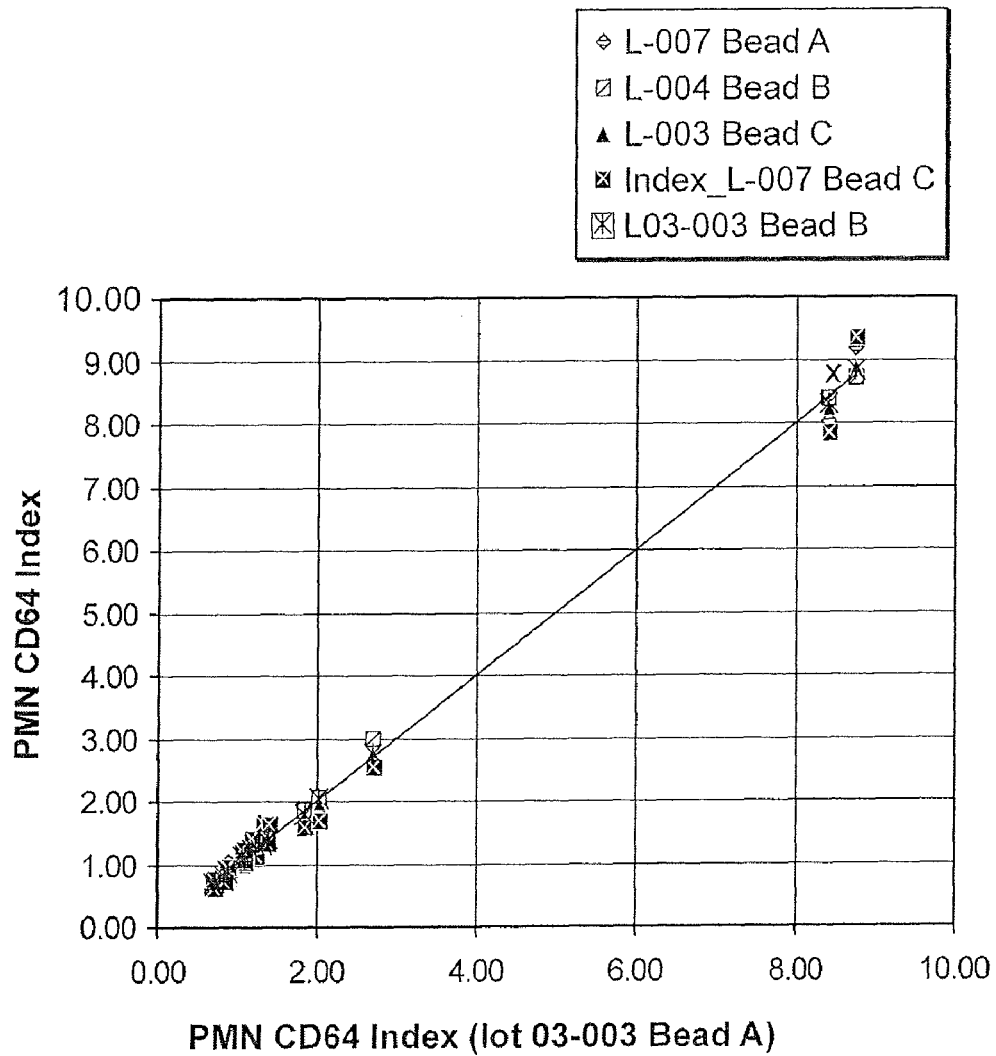
Figure 6C:
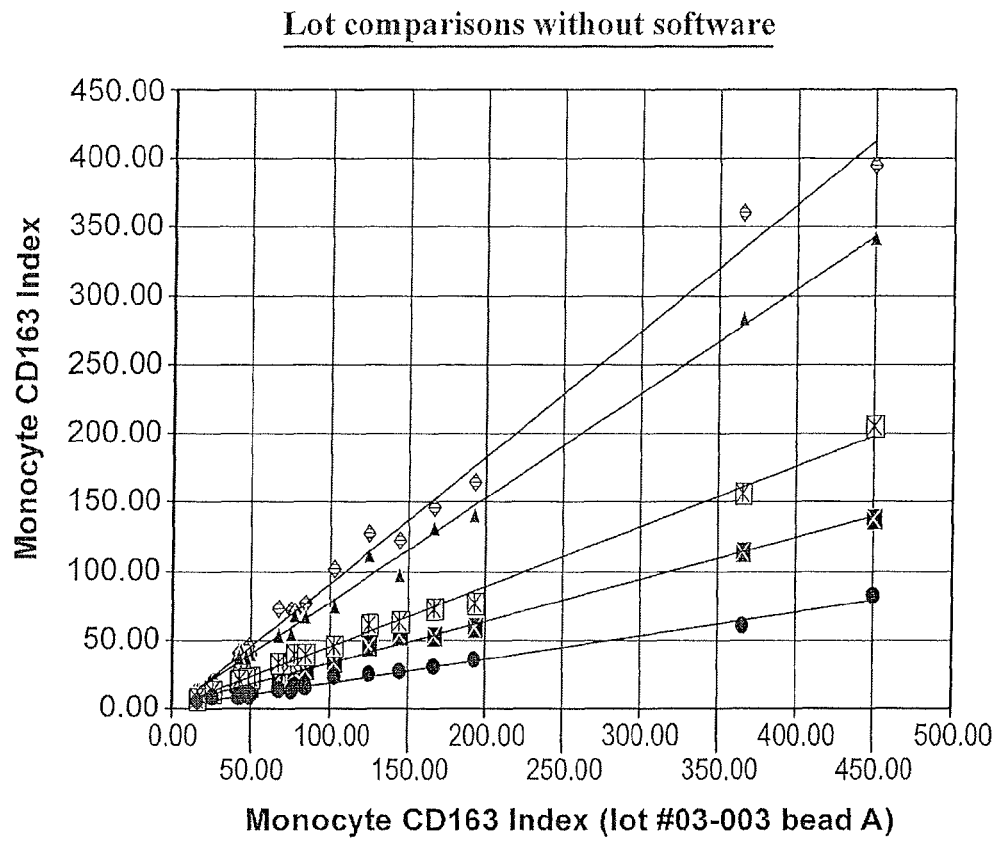
Figure 6D:
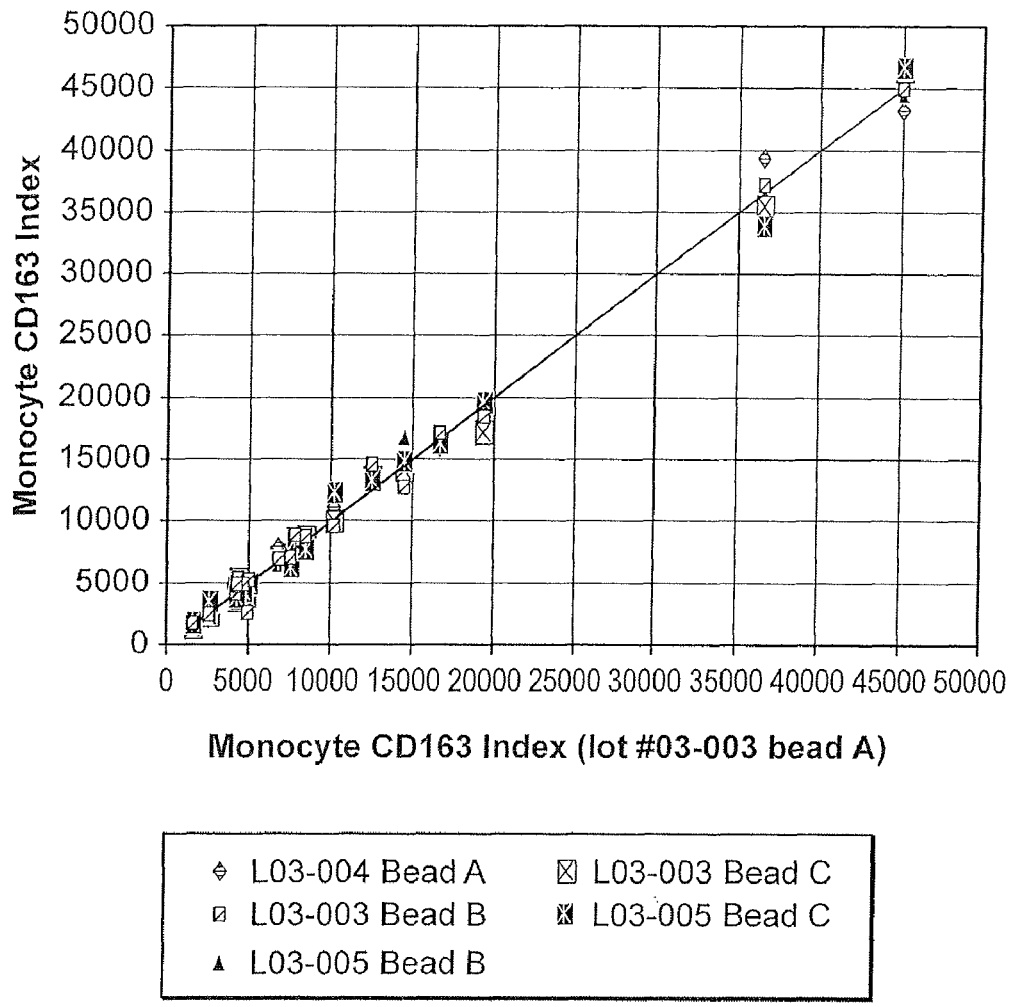

Studies with quantitative PMN CD64 measurements to date have indicated a high degree of specificity of greater than >98% for detection of systemic infection [35, 38, 41, 42, 54]. Interestingly along with the sensitivity for detecting the acute inflammatory response in conjunction with infection there is only a weak correlation with neutrophilia, sedimentation rate, and/or the presence of bands [35, 37], suggesting additional diagnostic information is afforded by CD64 measurements compared to standard laboratory testing modalities. Given there are multiple clinical explanations for elevated neutrophil counts, the potential for PMN CD64 expression to provide increased diagnostic sensitivity and specificity of infection, along with its ability to be performed in a clinical setting in a matter of hours, it should find clinical utility. Although clinical blood samples show a weak to moderate tendency for increased PMN CD64 expression in parallel with increasing neutrophil counts or band counts [35], clinical samples are consistently identified where PMN CD64 expression and leukocyte enumeration are discordant. Clinical samples with elevated absolute neutrophil counts, yet exhibiting normal CD64 expression, are commonly seen in three clinical situations. The situations being glucocorticoid or steroid therapy, the early post-surgical period, and chronic myeloproliferative disorders, in which treating physicians have learned to expect elevated PMN counts without the necessity for further therapeutic action or concern for infection. Observations to date of over 100 cases of chronic myeloid leukemia, chronic myeloproliferative disorders, and myelodysplastic syndromes have shown no increased CD64 expression on mature myeloid cells, except in such patients with documented evidence of infection or other recognizable or acute inflammatory process [45, 55, 56]. Thus, one additional potential clinical application of PMN CD64 expression could also be used to distinguish acute inflammatory responses from hematological malignancies resulting in neutrophilia. The corollary situation, where elevated PMN CD64 is observed in parallel with normal or decreased neutrophil counts is observed most commonly in clinical situations where patients have received myelosuppressive drugs, such as cancer chemotherapy, and yet have clinical symptoms or laboratory evidence of infection. Additional studies are required to validate the diagnostic utility of quantitative PMN CD64 measurements in specific clinical situations and to obtain FDA clearance as an in vitro diagnostic test. However, previous published work does indicate the level of PMN CD64 expression to correlate with both clinical probability of infection [35, 37-39, 41-43] and the type of infection (gram negative bacteria inducing higher PMN CD64 expression compared to gram positive bacteria) [42]. Additionally, as shown in FIG. 5 the magnitude of PMN CD64 expression appears lower in localized compared to systemic infections [37, 42]. In summary, the present invention relating to PMN CD64 diagnostic tests: 1) function in a triage role for patients having clinical symptoms suggestive of infection; 2) provide quantitative assessment of a systemic inflammatory response; 3) distinguish between inflammatory and leukemia-related causes for elevated leukocyte counts; 4) serve as a therapeutic monitor in patients with sepsis or infection.

Components Used in the Present invention Assay:

The following is a list of components and reagents that are used in the assay for inflammation and detection of tissue injury by quantifying CD64 expression in polymorphonuclear leukocytes:

(A) at least one or more monoclonal antibodies directed to CD64 conjugated to fluorescein isothiocyanate (FITC) or similar fluorochromes;

(B) at least one or more monoclonal antibodies directed to CD163 conjugated to phycoerythrin or similar fluorochromes;

(C) a suspension of polystyrene microbeads with at least one or more fluorochromes, one of which is identical to that conjugated to the CD64 monoclonal antibodies, environmentally sensitive to the same factors affecting the fluorescence of antibodies bound to cells, and traceable to an external standard, such as the NIST SRM 8640.

(D) the Leuko64 software, which allows for fluorescence value assignment to the microbeads and calibration of the quantitation of measurements of CD64 and CD163 expression and cellular cluster gating independent of user interaction.

Description of the Leuko64 Software:

Although the current assay for PMN CD64 can be performed using third party software capable of analyzing flow cytometric data, this approach leaves some degree of subjectivity in data analysis to end users, who typically have a range of skills. Thus, there remains the potential for errors or subjectivity in the assay result. Hence a preferable approach to minimize the user's subjectivity in data analysis and to streamline the assay is to include software for flow cytometric data with the CD64 assay. The Leuko64 CD64 assay kit includes a software that will indicate the outdate of the kit in parallel that of the assay reagent. The software has the ability to find cell clusters (lymphocytes, monocyte, and neutrophils) and perform automated data normalization and calculation of the PMN CD64 index. Additionally, the program can perform some specified analysis to serve as quality control functions, for example to validate that the monocyte population has the expected CD64 expression detected by the fluorescent antibody reagents, thus serving as an internal positive control for each specimen, and to validate that the lymphocyte population has no significant CD64 expression, thereby serving as an internal negative control for each specimen. Most importantly, the program allows for rapid data analysis from a variety of commercial clinical flow cytometry instruments, provide quality control related "flags" to the operator, and improve the standardization of data analysis to further minimize assay imprecision. A preferred embodiment of the invention is the integration of the software and bead fluorescence value assignment for CD64 and CD163 index values, which can be traceable to reference standards of fluorescence for specific fluorochromes. This value assignment of beads using a regression correlation between assay lots on biologic cell samples, such as blood leukocytes, provides for a low degree of imprecision between assay lots, thereby improving diagnostic utility in clinical practice.

EXEMPLIFICATION

The examples herein are given for the purpose of illustrating various embodiments of the invention and are not meant to limit the present invention in any fashion. All documents mentioned herein are incorporated by reference in their entirety.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

Example 1

Leukocyte CD64 Assay

The method for of flow cytometric analysis of blood samples for PMN CD64 is outlined briefly, and provided in detail by Davis et al [34-37, 40, 52, 53, 58, 59]. The current procedure for flow cytometric CD64 staining and analysis is as follows:

Trillium Diagnostics Leukocyte CD64 Assay Staining Procedure:

1. Dilute the 10× Trillium Lyse (Reagent B) 1:10 by mixing 1 part of the concentrated Reagent B with 9 parts filtered distilled water. Make a volume sufficient for anticipated number of tests (1.0 mL is required for each sample). The final pH of the diluted Reagent B should be 7.40±0.02; adjusted with NaOH or HCl if necessary. Diluted or 1× Trillium Lyse is stable for 1 week at room temperature (20-26° C.) or 30 days at 2-8° C.
2. Diluted lyse solution must be between 20° C. and 37° C. when used. Cold solution may result in poor lysis.
3. Aliquot 50 µL, of Leuko64 Reagent A into a 12×75 mm polystyrene tube.
4. Aliquot 50 µL, of mixed anticoagulated blood sample with white blood count <25×10$^9$ cells/L (dilute as required) to the tube containing Reagent A, gently mix or vortex, and incubate 10 minutes in the dark at room temperature.
5. Add 1.0 mL of 1× Trillium Lyse (diluted Reagent B) and thoroughly vortex. Let stand for 15 minutes in the dark at room temperature. Intermittent vortexing or mixing enhances lysis.
6. Add 5 µL, Leuko64 beads (Reagent C) to each tube, vortex, and analyze on flow cytometer using instrument set-up and analysis protocol below. Prepared samples should be held at 2-8° C., shielded from light until analyzed. Analysis should be performed within 24 hours of staining.

CD64 Instrument Calibration Bead Specimen:

Flow Cytometer Set-Up

Figure 7:
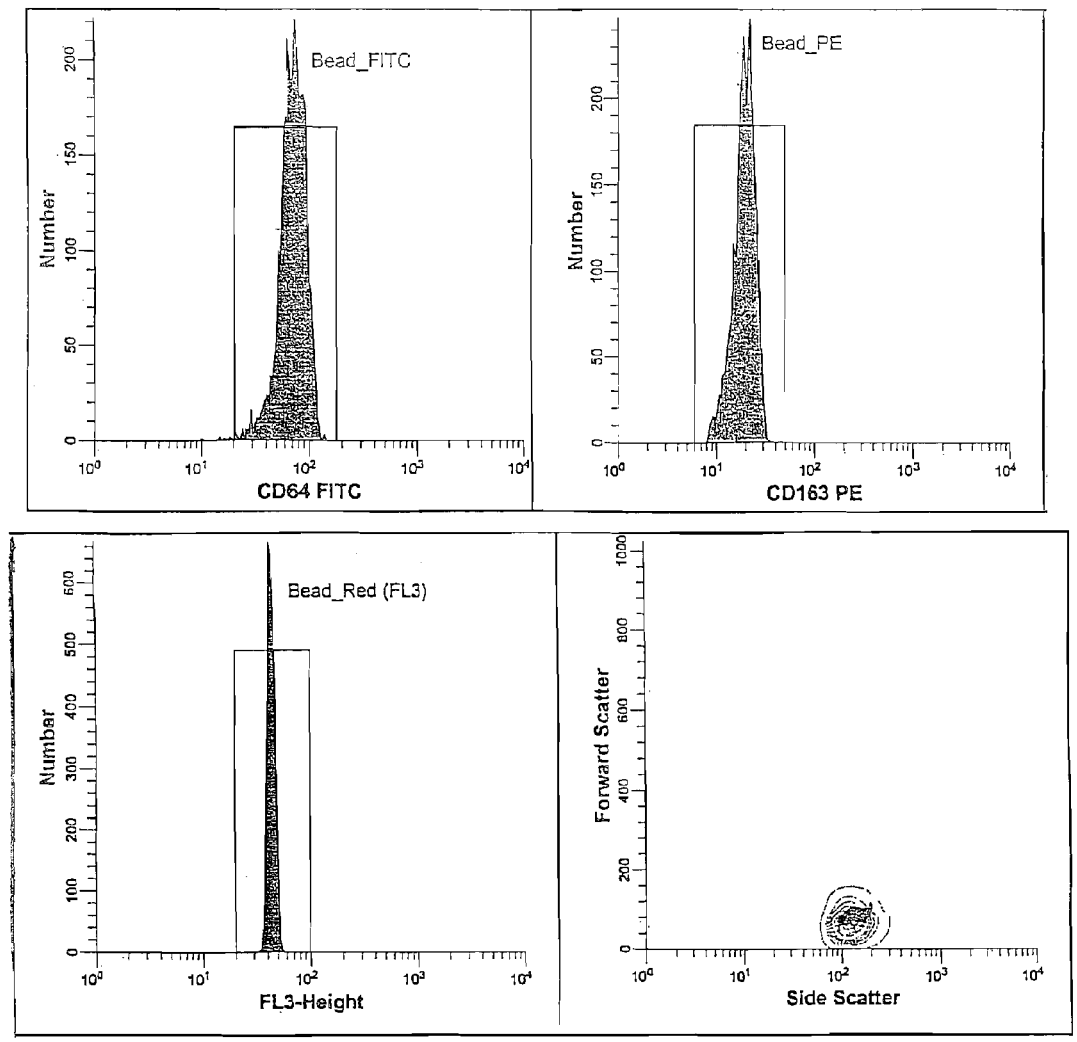
FIG. 7 is an illustration of an acquisition template in accord with the present invention.

1. Add 5 µL Leuko64 beads (Reagent C) to a tube containing 0.5 mL 1× Trillium Lyse (Reagent B diluted 1:10 with filtered distilled water, pH 7.40±0.02). This will be used to establish PMT voltage and scatter settings on the instrument.
2. Set up 4 two-parameter histograms:
   FS (lin) vs SS (log)
   CD64 FITC vs SS (log)
   CD163 vs SS (log)
   CD163 PE vs CD64 FITC
   And 3 one-parameter histograms:
   FL1—CD64 FITC
   FL2—CD163 PE
   FL3 (the PMT with filter setup able to detect 685 nM)
3. Turn OFF all compensation settings.
4. Run the bead suspension and make the following adjustments on the one-parameter histograms at 1024 channel resolution (see diagram):
   The center of the peak on the FL1 (FITC) axis should be at the end of the second decade of fluorescence intensity (MFI=~90).
   The center of the peak on the FL2 (PE) axis should be at a MFI=~20 (the first tic in the second decade of fluorescence intensity).
   The center of the peak on the FL3 axis should be mid-scale in second decade (MFI=~30).
5. On the FS vs SS histogram, the bead population should be positioned at the start of the third decade on log side scatter signal, and at channel 85-120 on forward or low angle scatter signal (on 256 scale use channel 20-25).
6. The threshold to exclude platelets and red cell debris should be set on SS (log) using lymphocytes. The discriminator to exclude debris and small particles should be set just to the left of the lymphocytes.
7. Acquisition and Storage settings should be adjusted to allow for collection of 50,000 ungated events. Setting resolution at 1024 is generally recommended, but is required when using Beckman Coulter FC-500™ or Becton Dickinson FACSCanto™ cytometers.
8. Save the settings and acquisition template as illustrated in FIG. 7.

Flow Cytometric Acquisition:

1. Perform the flow cytometer's daily instrument QC program and determine that the cytometer is ready for specimen acquisition.
2. Call up the CD64 protocol and run the stained specimens, including the beads.
3. Acquire at least 50,000 events and save list mode file for analysis with the Leuko64 software.

Analysis of Listmode Files:

1. Leuko64 software which is the software program used for the calculation of results.
2. Call up the bead mix listmode file and following the directions in the Leuko64 manual to initiate the Leuko64 Program
3. Call up the first listmode file to be analyzed. Confirm that the coarse gates around the leukocyte populations of lymphocytes, monocytes, and granulocytes are positioned correctly. If needed, the gate region can be adjusted to surround the appropriate cell population.
4. Analysis of specimen list mode files can be analyzed in a step by step fashion or by using the automated batch analysis function. Analysis results can be stored in the database and printing of the results is suggested to allow for subsequent documentation and review of the appropriate gating of the leukocyte subpopulations.
5. If the analysis is stopped due to either the lymphocyte or monocyte flag or warning dialog box appearing, the user should investigate possible causes for these adverse findings and consider reanalysis and/or restaining of the sample if necessary.

Limitations of Procedure:

1. It is essential to acquire adequate numbers of bead events (500 or more). Inadequate numbers of beads may cause invalidate CD96 and CD163 index results, which in turn will may result in false positive or negative results.
2. Some specimens do not lyse completely. However we are interested in the Neutrophil and bead populations, so the specimens can still be run. If the discriminator setting is not optimized, the listmode file may have insufficient bead or cell events to be statistically robust.
3. The assay requires sufficient anti-CD64 regent added to the tube, this could be verified by examination of the monocyte population, which can serve as an internal positive control as this populations should always stain "positive". If that is not the case, the software analysis monocyte flag will be activated.

Components of Invention
I. Reagent A

TABLE 2

| Leuko64 Reagent A: | Lot #L64-03-07 | Bottled conc (mg/mL) | Dilution Factor |
|---|---|---|---|
| Anti-CD64 clone 32.2 FITC (ATCC: HB9469) | 0206113.1T1 | 0.68 | diluted 1:272 |
| Anti-CD64 clone 22 FITC | 0104031.1T4 | 1.47 | diluted 1:980 |
| Anti-CD163 PE clone 48 or 158 (ATCC: HB 10714) | lot 0103203.2E5 | 0.93 | diluted 1:1190 |
| PBS w/0.1% BSA + 0.01% NaN3(Sigma) | | | |

Reagent A is used at a volume of 0.050 mL per test. Thus for a 250 test kit the total volume needed is 12.50 mL plus 1.25 mL for wastage. Bottle in two containers with a file volume of 7.5-10 mL. Bottles should be flat bottom amber glass composition with leak proof screw cap.

II. Leuko64 Reagent B: 10× Trillium Lyse Solution

| | | |
|---|---|---|
| NH$_4$Cl (potassium chloride) | 80.0 g | Sigma # P-9541 |
| EDTA Trisodium Salt | 10.0 g | Sigma # ED3SS |
| KH$_2$PO$_4$ (potassium phosphate) | 1.0 g | Sigma # P-5379 |
| QS to 1000 ml with reagent grade H$_2$O | | |
| Filter using 0.2 µm-pore vacuum filter | | Nalgene # 295 4520 |
| Adjust pH to 7.4 when solution reaches room temperature (use aliquots and aseptic technique To avoid contaminating the filtered solution) | | |
| Store in refrigerator at 2-8° C. | | |
| Expiration 12 months | | |

Reagent B is used at a volume of 1.0 mL per test after dilution (diluted form to have one week outdate). Thus for a 250 test kit the total volume needed is 25 mL plus 15 mL for wastage. Bottle in a container with a fill volume of 50 mL. Bottle can be of plastic composition (nalgene) with flat bottom and screw cap.

III. Leuko64 Reagent C: Calibrator Beads (NIST traceable reference material)

Polystyrene 5.2 pm beads tagged with a proprietary embedded red dye (starfire red) and surface coated with FITC (NTRM to NIST SRM 1932) suspended in an isotonic buffered solution containing BSA, sodium azide, Tween 20, pH 7.4. Final bead concentration at 4-6×10$^6$ per mL.

| Bead Diluent: | |
|---|---|
| Tween 20 | 10 uL |
| NaN3 | 0.013 g |
| PBS | 100 mL |
| pH = 7.4 | |
| Make a 1:20 dilution of each into PBS with 0.01% Tween and 2 mM NaN3. | |
| FITC Beads: | |
| Beads | 250 uL |
| Bead Diluent(above) | 4750 uL |

Reagent C is used at a volume of 0.005 mL per test. Thus for a 250 test kit the total volume needed is 1.25 mL plus 0.25 mL for wastage and instrument calibration.

Bottle in one container with a file volume of 2.0 mL. Bottles should be flat bottom amber glass composition with leak proof screw cap.

Reagent C will be provided for each lot following QC by Trillium Diagnostics, LLC and OEM manufacturing by Bangs, Inc.

IV. Leuko64 Software

Lot specific Leuko64 software will be provided in the kit in a standard CD disc. The CDs will be provided for packaging after QC validation by Trillium Diagnostics, LLC and Verity Software House. The software provides a lot-specific value assignment for the calibration beads and subsequently the final PMN and Monocyte CD64 Index values; this corrects for any lot-to-lot variations in bead production or monoclonal antibody fluorochrome labeling. Software validation procedure is in software folder.

All publications and patent applications disclosed herein, including U.S. Pat. Nos. 4,918,004 and 5,380,663 are incorporated into this application by reference in their entirety, which can be used in the instant invention.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed and equivalent within the spirit of the invention as defined by the scope of the claims.

REFERENCES

1. Balk, R. (2000) Severe sepsis and septic shock. *Critical Care Clinics* 16, 179-192.
2. Bernard, G., Vincent, J., Laterre, P., Dhainaut, J., Lopez-Rodriquez, A., Steingrub, J., Garber, G., Helterbrand, J., Ely, E., Fisher, C. (2001) Efficacy and safety of recombinant human activated protein C for severe sepsis. *New England Journal of Medicine* 344, 699-709.
3. Sands, K., Bates, D., Lanken, P., al., (1997) Epidemiology of sepsis syndrome in 8 academic medical centers. *Journal of Amereican Medical Association* 278, 234-240.
4. Opal, S., Cohen, J. (1999) Clinical gram-positive sepsis: does it fundamentally differ from Gram-negative bacterial sepsis? *Critical Care Medicine* 27, 1608-1616.
5. Karzai, W., Reinhart, K. (1998) Sepsis: definitions and diagnosis. *Int J Clin Pract Suppl* 95, 44-8.
6. Horn, K. (1998) Evolving strategies in the treatment of sepsis and systemic inflammatory response syndrome (SIRS). *QJM* 91, 265-77.
7. Fry, D. (2000) Sepsis syndrome. Am Surg 66, 126-32.
8. Fisher, C., Agosti, J., Opal, S., Lowry, S., Balk, R., Sadoff, J., Abraham, E., Schein, R., Benjamin, E. (1996) Treatment of septic shock with tumor necrosis receptor:Fc fusion protein. *New England Journal of Medicine* 334, 1697-1702.
9. Chiu, C.-H., Lin, T.-Y., Bullard, M. J. (1994) Application of criteria identifying febrile outpatient neonates at low risk for bacterial infections. *Pediatric Infectious Disease Journal* 13, 946-949.
10. Engle, W., Rosenfeld, C., Mouzinho, A., Risser, R., Zeray, F., Sanchez, P. (1997) Circulating neutrophils in septic preterm neonates: comparison of two reference ranges. *Pediatrics* 99, E10.
11. Pfitzenmeyer, P., Decrey, H., Auckenthaler, R., Michel, J. P. (1995) Predicting bacteremia in older patients. *Journal of American Geriatric Society* 43, 230-235.
12. Vermeulen, B., Morabia, A., Unger, P.-F. (1995) Influence of white cell count on surgical decision making in patients with abdominal pain in the right lower quadrant. *European Journal of Surgery* 161, 483-486.
13. Bentley, S. A. (1988) Alternatives to the neutrophil band count. Arch Pathol Lab Med 112, 883-884.
14. Ardron, M. J., Westengard, J. C., Dutcher, T. F. (1994) Band neutrophil counts are unnecessary for the diagnosis of infection in patients with normal leukocyte counts. *Am J Clin Pathol* 102, 646-649.
15. Bomela, H., Ballot, D., Cory, B., Cooper, P. (2000) Use of C-reactive protein to guide duration of empiric antibiotic therapy in suspected early neonatal sepsis. *Pediatr Infect Dis J* 19, 531-5.
16. Benitz, W., Han, M., Madan, A., Ramachandra, P. (1998) Serial serum C-reactive protein levels in the diagnosis of neonatal infection. *Pediatrics* 102, E41.
17. Clyne, B., Olshaker, J. (1999) The C-reactive protein. *J Emerg Med* 17, 1019-25.
18. Povoa, P., Almeida, E., Moreira, P., Fernandes, A., Mealha, R., Aragao, A., Sabino, H. (1998) C-reactive protein as an indicator of sepsis. *Intensive Care Med* 24, 1052-6.
19. Hogarth, M., Gallimore, R., Savage, P., Palmer, A., Starr, J., Bulpitt, C., Pepys, M. (1997) Acute phase proteins, C-reactive protein and serum amyloid A protein, as prognostic markers in the elderly inpatient. *Age Ageing* 26, 153-8.
20. Da Silva, O., Ohlsson, A., Kenyon, C. (1995) Accuracy of leukocyte indices and C-reactive protein for diagnosis of neonatal sepsis: a critical review. *Pediatr Infect Dis J* 14, 362-6.
21. Giannoudis, P., Smith, M., Evans, R., Bellamy, M., Guillou, P. (1998) Serum CRP and IL-6 levels after trauma. Not predictive of septic complications in 31 patients. *Acta Orthop Scand* 69, 184-8.
22. Al-Nawas, B., Krammer, I., Shah, P. (1996) Procalcitonin in diagnosis of severe infections. *Eur J Med Res* 1, 331-3.
23. Whang, K., Steinwald, P., White, J., Nylen, E., Snider, R., Simon, G., Goldberg, R., Becker, K. (1998) Serum calcitonin precursors in sepsis and systemic inflammation. *J Clin Endocrinol Metab* 83, 3296-301.
24. Somech, R., Zakuth, V., Assia, A., Jurgenson, U., Spirer, Z. (2000) Procalcitonin correlates with C-reactive protein as an acute-phase reactant in pediatric patients. *Isr Med Assoc J* 2, 147-50.
25. Kaftan, H., Kinney, J. (1998) Early onset neonatal bacterial infections. *Semin Perinatol* 22, 15-24.
26. Gerdes, J., Polin, R. (1998) Early diagnosis and treatment of neonatal sepsis. *Indian J Pediatr* 65, 63-78.
27. Carlet, J. (1999) Rapid diagnostic methods in the detection of sepsis. *Infect Dis Clin North Am* 13, 483-94, xi.
28. Antonelli, M., Raponi, G., Martino, P., Rosa, G., Conti, G., Jalouk, J., Gasparetto, A.
(1995) High IL-6 serum levels are associated with septic shock and mortality in septic patients with severe leukopenia due to hematological malignancies. *Scand J Infect Dis* 27, 381-4.
29. Marie, C., Fitting, C., Muret, J., Payen, D., Cavaillon, J. (2000) Interleukin 8 production in whole blood assays: Is interleukin 10 responsible for the downregulation observed in sepsis? *Cytokine* 12, 55-61.
30. Lehrnbecher, T., Schrod, L., Rutsch, P., Roos, T., Martius, J., von, S. H. (1996) Immunologic parameters in cord blood indicating early-onset sepsis. *Biol Neonate* 70, 206-12.
31. Ng, P., Cheng, S., Chui, K., Fok, T., Wong, M., Wong, W., Wong, R., Cheung, K. (1997) Diagnosis of late onset neonatal sepsis with cytokines, adhesion molecule, and C-reactive protein in preterm very low birthweight infants. *Arch Dis Child Fetal Neonatal Ed* 77, F221-7.
32. Laforgia, N., Coppola, B., Carbone, R., Grassi, A., Mautone, A., Iolascon, A. (1997) Rapid detection of neonatal sepsis using polymerase chain reaction. *Acta Paediatr* 86, 1097-9.
33. Weitkamp, J., Stuber, F., Bartmann, P. (2000) Pilot study assessing TNF gene polymorphism as a prognostic marker for disease progression in neonates with sepsis. *Infection* 28, 92-6.
34. Akerley, W. L., Guyre, P. M., Davis, B. H. (1991) Neutrophil activation through high-affinity Fc gamma receptor using a monomeric antibody with unique properties. *Blood* 77, 607-615.
35. Davis, B. H., Bigelow, N. C., Curnutte, J. T., Ornvold, K. (1995) Neutrophil CD64 expression: Potential diagnostic indicator of acute inflammation and therapeutic monitor of interferon-g therapy. *Lab Hematol* 1, 3-12.
36. Davis, B., Bigelow, N. (1996) Neutrophil CD64 (high affinity Fc receptor), indicator of acute inflammation: correlation with band counts and instrument flagging. *International Journal Hematology* 64, S157.
37. Davis, B. (1996) Quantitative neutrophil CD64 expression: Promising diagnostic indicator of infection or systemic acute inflammatory response. *Clinical Immunology Newsletter* 16, 121-130.
38. Davis, B., Wallace, P., Guyre, P. (1998) Pathophysiology of human Fc-gamma receptors in health and disease. In *Phagocyte Function: A Guide for Research and Clinical Evaluation* (J. Robinson and G. Babcock, eds), John Wiley & Sons, New York 47-76.
39. Fjaertoft, G., Hakans son, L., Ewald, U., Foucard, T., Venge, P. (1999) Neutrophils from term and preterm newborn infants express the high affinity Fcgamma-receptor I (CD64) during bacterial infections. *Pediatr Res* 45, 871-6.
40. Schiff, D., Rae, J., Martin, T., Davis, B., Curnutte, J. (1997) Increased phagocyte CD64 expression and improved Fc-receptor mediated phagocytosis following in vivo recombinant human interferon-g treatment of normal human subjects. *Blood* 90, 2987-94.
41. Guyre, P. M., Campbell, A. S., Kniffin, W. D., Fanger, M. W. (1990) Monocytes and polymorphonuclear neutrophils of patients with streptococcal pharyngitis express increased numbers of type I IgG Fc receptors. *J Clin Invest* 86, 1892-1986.
42. Herra, C. M., Keane, C. T., Whelan, A. (1996) Increased expression of Fc gamma receptors on neutrophils and monocytes may reflect ongoing bacterial infection. *Journal of Medical Microbiology* 44, 135-40.
43. Leino, L., Sorvajarvi, K., Katajisto, J., Laine, M., Lilius, E., Pelliniemi, T., Rajamaki, A., Silvoniemi, P., Nikoskelainen, J. (1997) Febrile infection changes the expression of IgG Fc receptors and complement receptors in human neutrophils in vivo. *Clin Exp Immunol* 107, 37-43.
44. Turzanski, J., Crouch, S. P., Andrews, M., Rose, M., Finch, R., Burden, R., Holliday, M., Fletcher, J. (1998) Effects of r-metHuG-CSF on polymorphonuclear leucocyte kinetics and function in patients on continuous ambulatory peritoneal dialysis. *British Journal of Haematology* 103, 387-96.
45. Trillium Diagnostics (1996-2001) unpublished or proprietary information.
46. Sacks, G., Studena, K., Sargent, K., Redman, C. (1998) Normal pregnancy and preeclampsia both produce inflammatory changes in peripheral blood leukocytes akin to those of sepsis [see comments]. *Am J Obstet Gynecol* 179, 80-6.

47. Davis, D., Kaufmann, R., Moticka, E. (1998) Nonspecific immunity in pregnancy: Monocyte surface receptor expression and function. *Journal of Reproductive Immunology* 40, 119-128.
48. Pan, L. Y., Mendel, D. B., Zurlo, J., Guyre, P. M. (1990) Regulation of the steady state level of Fc gamma RI mRNA by IFN-gamma and dexamethasone in human monocytes, neutrophils, and U-937 cells. *J Immunol* 145, 267-75.
49. Petroni, K. C., Shen, L., Guyre, P. M. (1988) Modulation of human polymorphonuclear leukocyte IgG Fc receptors and Fc receptor-mediated functions by IFN-gamma and glucocorticoids. *J Immunol* 140, 3467-72.
50. Cassatella, M. A., Flynn, R. M., Amezaga, M. A., Bazzoni, F., Vicentini, F., Trinchieri, G. (1990) Interferon gamma induces in human neutrophils and macrophages expression of the mRNA for the high affinity receptor for monomeric IgG (Fc gamma R-I or CD64). *Biochem Biophys Res Commun* 170, 582-8.
51. Roilides, E., Holmes, A., Blake, C., Pizzo, P., Walsh, T. J. (1995) Effects of granulocyte colony-stimulating factor and interferon-g on antifungal acitivity of human polymorphonuclear neutrohils against pseudohyphae of different medically important Candida species. *Journal of Leukocyte Biology* 57, 651-656.
52. Pizza, F., Davis, B., Hendrickson, S., Mitchell, J., Pace, J., Bigelow, N., DiLauro, P., Nagieri, T. (1996) Adaptation to eccentric exercise: effect on CD64 and CD11b/CD18 expression. *J Applied Physiology* 80, 47-55.
53. Pizza, F., Mitchell, J., Davis, B., Starling, R., Holtz, R., Bigelow, N. (1995) Exercise-induced muscle damage: effect on circulating leukocyte and lymphocyte subsets. *Med Sci Sports Exercise* 27, 363-370.
54. Simms, H. H., D'Amico, R. (1994) Polymorphonuclear leukocyte dysregulation during the systemic inflammatory response syndrome. *Blood* 83, 1398-407.
55. Westwood, N. B., Copson, E. R., Page, L. A., Mire-Sluis, A. R., Brown, K. A., Pearson, T. C. (1995) Activated phenotype in neutrophils and monocytes from patients with primary proliferative polycythaemia. *Journal of Clinical Pathology* 48, 525-30.
56. Felzmann, T., Gadd, S., Majdic, 0., Maurer, D., Petera, P., Smolen, J., Knapp, W. (1991) Analysis of function-associated receptor molecules on peripheral blood and synovial fluid granulocytes from patients with rheumatoid and reactive arthritis. *J Clin Immunol* 11, 205-12.
57. Wenzel, R., Edmond, M. (2000) Managing Antibiotic Resistance. *New England Journal of Medicine* 343, 1961-1963.
58. Davis, B., Bigelow, N. (1994) CD 64 (high affinity Fc receptor) is an indicator of neutrophil activation. *Cytometry Suppl.* 7, 29.
59. Davis, W., Harrison, P. T., Hutchinson, M. J., Allen, J. M. (1995) Two distinct regions of FC gamma RI initiate separate signalling pathways involved in endocytosis and phagocytosis. *Embo J* 14, 432-41.
60. Michon, J. M., Gey, A., Moutel, S., Tartour, E., Meresse, V., Fridman, W., Teillaud, J. L. (1998) In vivo induction of functional Fc gammaRl (CD64) on neutrophils and modulation of blood cytokine mRNA levels in cancer patients treated with G-CSF (rMetHuG-CSF). *British Journal of Haematology* 100, 550-6.
61. Wiener, E., Allen, D., Porter, R., Wickramasinghe, S., Porter, J., Chinprasertsuk, S., Siripanyaphinyo, U., Pattanapanyasat, K., Fucharoen, S., Wanachiawanawin, W. (1999) Role of FcgRI (CD64) in erythrocyte elimination and its up-regulation in thalassaemia. *British Journal of Haematology* 106, 923-930.
62. Repp, R., Valerius, T., Sendler, A., Gramatzki, M., Iro, H., Kalden, J. R., Platzer, E. (1991) Neutrophils express the high affinity receptor for IgG (Fc gamma RI, CD64) after in vivo application of recombinant human granulocyte colony-stimulating factor. *Blood* 78, 885-9.
63. Moallem, H., Kalayci, O., Homel, P., Fikrig, S., Chice, S., Durkin, H., Michl, J. (2000) Expression of Fc(gamma)r1 (CD64) on polymorphonuclear leucocytes during progression to acquired immunodeficiency syndrome in perinatally human immunodeficiency virus-infected children. *Scand J Immunol* 52, 184-9.
64. Ohsaka, A., Saionji, K., Takagi, S., Igari, J. (1996) Increased expression of the high-affinity receptor for IgG (FcRI, CD64) on neutrophils in multiple myeloma. *Hematopathology & Molecular Hematology* 10, 151-60.
65. Quayle, J. A., Watson, F., Bucknall, R. C., Edwards, S. W. (1997) Neutrophils from the synovial fluid of patients with rheumatoid arthritis express the high affinity immunoglobulin G receptor, Fc gamma RI (CD64): role of immune complexes and cytokines in induction of receptor expression. *Immunology* 91, 266-73.
66. Kerst, J. M., van de Winkel, J. G. J., Evans, A. H., de Haas, M., Slaper-Cortenbach, I. C., de Wit, T. P., von dem Borne, A. E., van der Schoot, C. E., van Oers, R. H. (1993) Granulocyte colony-stimulating factor induces hFc gamma RI (CD64antigen)-positive neutrophils via an effect on myeloid precursor cells. *Blood* 81, 1457-1464.
67. Krasinskas, A. M., Wasik, M. A., Kamoun, M., Schretzenmair, R., Moore, J., Salhany, K. E. (1998) The usefulness of CD64, other monocyte-associated antigens, and CD45 gating in the subclassification of acute myeloid leukemias with monocytic differentiation. *American Journal of Clinical Pathology* 110, 797-805.
68. Valerius, T., Repp, R., de Wit, T. P., Berthold, S., Platzer, E., Kalden, J. R., Gramatzki, M., van de Winkel, J. G. (1993) Involvement of the high-affinity receptor for IgG (Fc gamma RI; CD64) in enhanced tumor cell cytotoxicity of neutrophils during granulocyte colony-stimulating factor therapy. *Blood* 82, 931-9.
69. Fadlon, E., Vordermeier, S., Pearson, T. C., Mire-Sluis, A. R., Dumonde, D. C., Phillips, J., Fishlock, K., Brown, K. A. (1998) Blood polymorphonuclear leukocytes from the majority of sickle cell patients in the crisis phase of the disease show enhanced adhesion to vascular endothelium and increased expression of CD64. *Blood* 91, 266-74.
70. Schwartz, A., Fernandez-Repollet, E., Vogt, R., Gratama, J. (1996) Standardizing flow cytometry: Construction of a standardizing fluorescence calibration plot using matching spectral calibrators. *Cytometry* 26, 22-31.
71. Davis, K., Abrams, B., Iyer, S., Hoffman, R., Bishop, J. (1998) Determination of CD4 antigen density on cells: role of antibody valency, avidity, clones, and conjugation. *Cytometry* 33, 197-205.
72. Lenkei, R., Andersson, B. (1995) Determination of the antibody binding capacity of lymphocyte membrane antigens by flow cytometry in 58 blood donors. *Journal of Immunological Methods* 183, 267-277.
73. Masuda, M., Roos, D. (1993) Association of all three types of Fc gamma R (CD64, CD32, and CD16) with a gamma-chain homodimer in cultured human monocytes. *J Immunol* 151, 7188-95.
74. Maeda, M., van Schie, R., Yuksel, B., Greenough, A., Fanger, M. W., Guyre, P. M., Lydyard, P. M. (1996) Differential expression of Fc receptors for IgG by monocytes and granulocytes from neonates and adults. *Clin Exp Immunol* 103, 343-7.

75. Dougherty, G., Selvendran, Y., Murdoch, S., Palmer, D., Hogg, N. (1987) The human mononuclear phagocyte high affinity receptor, RcRI, defined by a monoclonal antibody 10.1. *European Journal of Immunology* 17, 1453-1459.
76. Guyre, P. M., Graziano, R. F., Vance, B. A., Morganelli, P. M., Fanger, M. W. (1989) Monoclonal antibodies that bind to distinct epitopes on Fc gamma RI are able to trigger receptor function. *J Immunol* 143, 1650-5.
77. van de Winkel, J. G. J., Anderson, C. L. (1991) Biology of human immunoglobulin G Fc receptors. *J Leukoc Biol* 49, 511-524.
78. Deo, Y., Graziano, R., Repp, R., van de Winkel, J. (1997) Clinical significance of IgG Fc receptors and FcgR-directed immunotherapies. *Immunology Today* 18, 127-135.
79. van de Winkel, J., de Wit, T., Ernst, L. K., Capel, P. J., Ceuppens, J. L. (1995) Molecular basis for a familial defect in phagocyte expression of IgG receptor I (CD64). *J Immunol* 154, 2896-903.

We claim:

1. A kit for automated performance of an integrated software-fluorescent microbeads standards system, said kit comprising:

monoclonal antibodies labeled with one or more fluorochromes;

microbeads comprising the same one or more fluorochromes used for labeling the antibodies; and a computer readable non-transitory medium containing a software program for implementation on a computer, wherein:

the software program is matched to specific lots of microbead standards and fluorescent-labeled mixtures of monoclonal antibodies and includes information on the fluorescence intensity of each population of microbeads;

for each batch of microbeads and fluorescent reagents, the associated software program includes information on the fluorescence intensity of each population of microbeads within the batch;

the software program takes information on a suspension of the microbeads and the fluorescent labeled antibodies bound to cells from a flow cytometer and analyzes data, smooth curves, calculates new parameters, provides quality control measures and indicates the expiration of the microbeads and fluorescent labeled antibodies;

the software program alerts the operator and further interrogates the users to verify the assay lot in use and the type of flow cytometric instrument employed as part of the specimen analysis;

the software program records results in a cumulative file history to provide comprehensive documentation of an instrument's performance;

the software program normalizes the bias or difference in fluorescent expression between different production lots by a factor determined by regression analysis between lots and changes in the fluorescent value assigned to the microbeads within the software program;

the software program monitors comparisons of data of different microbead production lots and fluorescent labeled antibody production lots on different biologic samples to determine whether the microbeads are within the required range of fluorescence intensity to insure that levels of imprecision between lots is $\leq 5\%$; and if desired, determines the actual amount of fluorescent antibody bound by the specimen cells through the use of external standards.

* * * * *